United States Patent
Fan et al.

(10) Patent No.: US 7,863,337 B2
(45) Date of Patent: Jan. 4, 2011

(54) USE OF TRIACONTANOL IN PREPARATION OF MEDICAMENTS FOR TREATMENT OF CANCERS

(75) Inventors: Xiane Fan, Kunming Longjin Pharmaceutical Co. Ltd., Xiaduan Wujia Pile, Xinwen Road, Kunming, Yunnan (CN); Renwei Zhang, Kunming (CN); Huijia Cheng, Kunming (CN)

(73) Assignee: Xiane Fan, Kunming (CN)

( * ) Notice: Subject to any disclaimer, the term of this patent is extended or adjusted under 35 U.S.C. 154(b) by 0 days.

(21) Appl. No.: 12/515,801

(22) PCT Filed: Sep. 30, 2007

(86) PCT No.: PCT/CN2007/002875

§ 371 (c)(1),
(2), (4) Date: May 21, 2009

(87) PCT Pub. No.: WO2008/061429

PCT Pub. Date: May 29, 2008

(65) Prior Publication Data

US 2010/0041924 A1    Feb. 18, 2010

(30) Foreign Application Priority Data

Nov. 23, 2006    (CN) .................. 2006 1 0048846

(51) Int. Cl.
*A61K 31/045* (2006.01)
(52) U.S. Cl. ...................................... 514/724
(58) Field of Classification Search ................. 514/724
See application file for complete search history.

(56) References Cited

U.S. PATENT DOCUMENTS

| | | | | | |
|---|---|---|---|---|---|
| 5,283,328 | A | * | 2/1994 | Kovacs et al. ............. 536/120 |
| 5,856,316 | A | * | 1/1999 | Laguna Granja et al. .... 514/164 |
| 6,596,776 | B2 | * | 7/2003 | Gamble et al. .............. 514/724 |
| 2006/0020045 | A1 | * | 1/2006 | Berlin ........................ 514/724 |
| 2006/0057237 | A1 | * | 3/2006 | Darro et al. ................. 424/777 |

* cited by examiner

*Primary Examiner*—Sikarl A Witherspoon

(57) ABSTRACT

Use of triacontanol in preparation of human medicaments for treatment of cancers, especially liver cancer, intestinal cancer, and lung cancer. Triacontanol can be formulated into many formulations, such as oral tablets, capsules, drop pills, sustained-released formulation, injectable solution, injectable powder, suspension, and emulsion.

8 Claims, No Drawings

USE OF TRIACONTANOL IN PREPARATION OF MEDICAMENTS FOR TREATMENT OF CANCERS

FIELD OF THE INVENTION

The present invention relates to use of a known chemical substance in preparation of human medicaments.

BACKGROUND OF THE INVENTION

Triacontanol, with a molecular formula of $C_{30}H_{62}O$, a structural formula of $CH_3$—$(CH_2)_{28}$—$CH_2$—$OH$, has been reported a lot in the prior art. All the reports focus on usage of triacontanol as a growth regulator and a nutritional agent for vegetables, fruits, plants and grain crops, and some reports also refer it as a pesticide. No study about use of triacontanol in preparation of human medicaments has been reported.

SUMMARY OF THE INVENTION

The object of the present invention is to overcome the above-mentioned shortage in the prior art and provide a new use of triacontanol in preparation of human medicaments for treatment of cancers.

The present invention relates to a use of triacontanol in preparation of human medicaments for treatment of liver cancers.

The present invention relates to a use of triacontanol in preparation of human medicaments for treatment of intestinal cancers.

The present invention relates to a use of triacontanol in preparation of human medicaments for treatment of lung cancers.

In order to help well understanding the substance of the present invention, pharmacological tests of triacontanol and their results are provided to explain the new use of triacontanol in the pharmaceutical field.

In vivo antitumor test of triacontanol (No. 352B):

Antitumor curative effect tests against murine hepatoma $H_{22}$, intestinal cancer $C_{26}$ by a thixotropic oil suspension, an emulsion, and a finish oil of triacontanol, and antitumor curative effect test against Lewis lung cancer by an emulsion of triacontanol Experiment method: Edema and pain inhibition effect of the tumor models of murine hepatoma $H_{22}$, intestinal cancer $C_{26}$ and Lewis lung cancer by hypodermic inoculating in the murine in vivo A cancer cell suspension is prepared from the tumor source by homogenate technique, and then is inoculated subcutaneously under the armpit. After 24 hours, medication is administrated according to a predesigned scheme, and finally, an inhibition rate statistic against the tumor is obtained by comparing with a negative control group. The results are shown in Table 1.

TABLE 1

Curative effect test against murine hepatoma $H_{22}$ by gavaging a thixotropic oil suspension of triacontanol

| Sample | Dosage Mg/kg/d | Administration scheme | Amount of the animal (unit) at the beginning/at last | Weight of the animal (g) at the beginning/at last | Weight of the tumor (g) X ± SD | Inhibition rate % |
|---|---|---|---|---|---|---|
| 352B thixotropic agent | 200 | Igx6qd | 10/10 | 20.9/27.3 | 1.45 ± 0.26** | 55.67 |
| 352B thixotropic agent | 150 | Igx6qd | 10/10 | 21.0/27.8 | 1.61 ± 0.17** | 46.33 |
| 352B thixotropic agent | 100 | Igx6qd | 10/10 | 20.7/27.6 | 1.75 ± 0.21** | 41.67 |
| 352B thixotropic agent | 50 | Igx6qd | 10/10 | 21.0/28.0 | 2.14 ± 0.28 | 28.0 |
| DDP | 7 | igx2 | 10/10 | 21.4/25.4 | 1.269 ± 0.13** | 91.0 |
| Negative control group | Blank solvent | igx6qd | 24/20 | 20.7/28.6 | 3.00 ± 0.34 | |

**compared with the negative control group, p value <0.01.

TABLE 2

Curative effect test against murine Lewislung cancer (hypodermically inoculated) by intravenous administration of a triacontanol emulsion

| Sample | Dosage Mg/kg/d | Administration scheme | Amount of the animal (unit) at the beginning/at last | Weight of the animal (g) at the beginning/at last | Weight of the tumor (g) X ± SD | Inhibition rate % |
|---|---|---|---|---|---|---|
| 352B emulsion | 200 | ivx10qd | 10/10 | 1.2/23.2 | 1.27 ± 0.18** | 54.15 |
| 352B emulsion | 150 | ivx10qd | 10/10 | 19.2/23.8 | 1.30 ± 0.15** | 53.07 |

TABLE 2-continued

Curative effect test against murine Lewislung cancer (hypodermically inoculated) by intravenous administration of a triacontanol emulsion

| Sample | Dosage Mg/kg/d | Administration scheme | Amount of the animal (unit) at the beginning/at last | Weight of the animal (g) at the beginning/at last | Weight of the tumor (g) X ± SD | Inhibition rate % |
|---|---|---|---|---|---|---|
| 352B emulsion | 100 | ivx10qd | 10/10 | 19.3/24.2 | 1.71 ± 0.17** | 38.27 |
| 352B emulsion | 50 | ivx10qd | 10/10 | 19.6/24.3 | 1.82 ± 0.15** | 34.30 |
| DDP | 7 | ipx2 | 10/10 | 19.2/20.9 | 0.278 ± 0.14** | 89.00 |
| Negative control group | Blank solvent | ivx10qd | 20/20 | 19.5/25.0 | 2.77 ± 0.18 | |

**compared with the negative control group, p value <0.01.

TABLE 3

Curative effect test against murine hepatoma $H_{22}$ (inoculated under the armpit) by gavaging a triacontanol oil agent

| Group | Dosage (mg/kg) | Amount of the animal (unit) | Weight (g) before administration | Weight (g) After administration | Weight of the tumor (g) | Inhibition rate (%) | P value |
|---|---|---|---|---|---|---|---|
| NS | Equivalent volume | 8 | 18.89 ± 1.31 | 23.94 ± 2.75 | 1.52 ± 0.64 | — | — |
| DDP | 0.001 | 8 | 19.16 ± 1.47 | 49.26 ± 3.39 | 0.31 ± 0.19 | 79.76 | <0.01△ |
| Menstruum | Equivalent volume | 8 | 19.09 ± 1.29 | 23.42 ± 2.10 | 1.38 ± 0.62 | — | |
| 352-B low dosage | 50 | 8 | 19.07 ± 1.14 | 23.51 ± 1.99 | 0.72 ± 0.38 | 48.13 | <0.01* |
| 352-B middle dosage | 100 | 8 | 19.36 ± 1.76 | 23.20 ± 2.86 | 0.57 ± 0.28 | 58.95 | <0.01* |
| 352-B high dosage | 150 | 8 | 19.25 ± 1.31 | 23.52 ± 2.36 | 0.49 ± 0.25 | 64.59 | <0.01* |

Note:
△compared with the NS control group;
*compared with the menstruum control group.

TABLE 4

Effect to the thymus index and spleen index of murine by gavaging a triacontanol oil agent

| Group | Dosage (mg/kg) | Weight of thymus (mg) | Thymus index (g/10 g body weight) | P value | Weight of spleen (mg) | Spleen index (g/10 g body weight) | P value |
|---|---|---|---|---|---|---|---|
| NS | Equivalent volume | 104.23 ± 20.34 | 47.72 ± 9.49 | | 188.04 ± 43.69 | 84.95 ± 12.94 | |
| DDP | 0.001 | 59.61 ± 22.45 | 30.66 ± 8.06 | <0.05△ | 88.90 ± 27.79 | 46.05 ± 8.18 | <0.01△ |
| Menstruum | Equivalent volume | 95.86 ± 18.83 | 43.76 ± 9.18 | | 148.21 ± 31.97 | 66.94 ± 12.04 | |
| 352-B low dosage | 50 | 102.14 ± 15.90 | 44.96 ± 6.72 | >0.05* | 153.52 ± 35.62 | 67.11 ± 13.67 | >0.05* |
| 352-B middle dosage | 100 | 86.87 ± 16.44 | 38.71 ± 8.08 | >0.05* | 139.98 ± 41.62 | 62.12 ± 17.54 | >0.05* |
| 352-B high dosage | 150 | 86.86 ± 16.14 | 37.70 ± 6.73 | >0.05* | 151.26 ± 32.16 | 65.71 ± 12.34 | >0.05* |

Note:
△compared with the NS control group;
*compared with the menstruum control group.

TABLE 5

Curative effect test against murine intestinal cancer C26 (hypodermically inoculated) by gavaging a 352B oil agent

| sample | Dosage mg/kg/d | Administration scheme | Amount of the animal (unit) at the beginning/at last | Weight of the animal (g) at the beginning/at last | Weight of the tumor (g) X ± SD | Inhibition rate % |
|---|---|---|---|---|---|---|
| 352B oil agent | 150 | igx10qd | 10/10 | 19.3/25.1 | 1.43 ± 0.17** | 46.24 |
| 352B oil agent | 100 | igx10qd | 10/10 | 19.4/25.3 | 1.57 ± 0.18** | 40.98 |
| 352B oil agent | 50 | igx10qd | 10/10 | 19.7/25.5 | 1.76 ± 0.17** | 33.83 |
| DDP | 7 | ipx2 | 10/10 | 19.1/24.1 | 0.346 ± 0.13** | 86.99 |
| Negative control group | Blank solvent | igx10qd | 20/20 | 19.5/25.7 | 2.66 ± 0.22 | |

Note:
**compared with the negative control group, p value <0.01.

The above tests prove that the triacontanol has prominent antitumor effect and obvious dose-effect relationship, and hasn't obvious effect to the important immune organ (such as thymus and spleen) of the tumor-bearing mice.

The present invention has the following advantages:

1. The present invention digs a new medical usage of triacontanol which is a known compound and exploits a new application field.

2. The triacontanol according to the present invention is safe and nontoxic, and has strong pharmacological action and good medical application prospect.

3. The triacontanol according to present invention may be formulated into many different formulations, such as oral tablets, capsules, drop pills, sustained-released formulation, injectable solution, injectable powder, injectable suspension, and injectable emulsion. The dosage is Oral Administration: 200 mg-1000 mg/day·person; Injection: 100 mg-600 mg/day·person.

DETAILED DESCRIPTION OF THE PREFERRED EMBODIMENT

Embodiment 1

Preparation of a capsule: 100 g triacontanol is dissolved into a proper amount of peanut oil, at the same time, starch and a spot of cyclodextrin for granulating is added. The mixture are launched into a mixer to mix uniformly and dried at 60° C., then sifted by an 80-mesh sieve. Granules made from the above-mentioned triacontanol and its auxiliary material is filled into a hollow capsule (Hard capsules of standard 2 or 3) by employing an automatic capsule filling machine.

We claim:

1. A method of preparing human medicaments for cancer treatment, comprising the following steps:
   dissolving triacontanol as the only anti-cancer component into peanut oil;
   adding starch and cyclodextrin for granulating;
   launching into a mixer to mix uniformly and then drying; and
   then bolting, and filling granules.

2. The method according to claim 1, wherein the cancer is liver cancer.

3. The method according to claim 1, wherein the cancer is intestinal cancer.

4. The method according to claim 1, wherein the cancer is lung cancer.

5. A method of treating cancer, comprising the following steps:
   preparing a human medicament including triacontanol as the only anti-cancer component; and
   administrating the human medicament to a patient having a cancer.

6. The method according to claim 5, wherein the cancer is liver cancer.

7. The method according to claim 5, wherein the cancer is intestinal cancer.

8. The method according to claim 5, wherein the cancer is lung cancer.

* * * * *